US00PP10740P

United States Patent [19]

Lane

[11] Patent Number: Plant 10,740

[45] Date of Patent: Dec. 29, 1998

[54] APPLE TREE NAMED 'SILKEN'

[75] Inventor: W. David Lane, Summerland, Canada

[73] Assignee: Okanagan Plant Improvement Co. Ltd.

[21] Appl. No.: 879,123

[22] Filed: Jun. 19, 1997

[51] Int. Cl.[6] ..... A01H 5/00

[52] U.S. Cl. ..... Plt./35.1

[58] Field of Search ..... Plt./35.1

*Primary Examiner*—Howard J. Locker
*Assistant Examiner*—Melissa L. Kimball

[57] ABSTRACT

The present invention relates to an apple tree and more particularly to a new and distinct variety broadly characterized by its spur type moderately vigorous, productive, precocious and regular bearing tree. The fruit matures under the described conditions approximately the first week of September at Summerland British Columbia. The fruit is medium-sized, oblong to globose truncate in shape with translucent, ivory to soft yellow skin color, sweet in flavor, and has white, crisp, firm, and very juicy flesh. The variety was developed from a seeding from a controlled cross of the seed parent 'Honeygold' and the pollen 'Sunrise'.

3 Drawing Sheets

BACKGROUND OF THE INVENTION

This invention relates to apple trees and particularly to a seedling apple tree from a controlled cross made by the Pacific Agri-Food Research and Agriculture Centre Summerland apple breeding program located at Summerland, British Columbia, Canada.

The Agriculture and Agri-Food Canada research facility at Summerland was established in 1914. Orginally called the Dominion Experimental Farm at Summerland, the name was changed to the Summerland Research Station in 1959, the Summerland Research Centre in 1994 and to the Pacific Agri-Food Research Centre Summerland in 1996. The tree fruit breeding program was established in 1924 to provide new varieties for the tree fruit industry of British Columbia, Canada, and the world. The breeding program at Summerland has produced several tree fruit varieties including 'Spartan', 'Summerred' and 'Sunrise' apples (all unpatented varieties) and 'Van', 'Lapins' and 'Sweetheart' cherries. The tree fruit breeders typically produce several thousand hybrid seedlings each year. Under the direction of the breeder the technician, as part of his duties, propagates the seedlings, by budding onto rootstocks, to induce earlier fruiting, in "seedling" fields. Upon fruiting, the varieties are evaluated for appearance, taste, and texture. Harvest indices, disease susceptibility and growth habit are evaluated in the field. Promising seedlings are re-propagated, in replications of four to six trees, by budding or grafting onto rootstocks and planted out as first selections in variety evaluation plots. The reproductions are evaluated for varietal stability, disease susceptibility, and fruit and tree quality. The most promising selections are repropagated and planted out in randomized evaluation plots complete with reference varieties (commercial varieties). Upon fruiting, selections are evaluated for varietal stability in the field, and for taste, texture and appearance of the fruit, in "in-house" sensory evaluation panels. The new varieties are compared to reference varities to establish uniqueness. The present invention relates to a new and distinct variety of apple tree which was named 'Silken' in January of 1997. The original cross was made in 1982 by breeder Dr. W. D. Lane. The variety is the offspring of the seed parent 'Honeygold' (a cross of 'Golden Delicious' and 'Haralson' released from the University of Minnesota in 1969) and the pollen parent 'Sunrise' (a cross of the seed parent '10C-10-19' from the Pacific Agri-Food Research Centre Summerland ×'PCF-3-120' (a numbered selection from the Purdue Central farm)). The seedling was propagated, by budding, onto rootstocks in "seedling" plots, to induce earlier fruiting in 1985 and given the breeders's reference number '8S-4-33'. '8S-4-33' was selected by Lane and reproduced by budding in 1988. Six propagations were planted in second selection variety test plots in 1990. The fruit and plant characteristics were true to the original tree in all respects. The variety was selected on the criteria of appearance, eating quality, and early harvest date of the fruit. '8S-4-33' was re-propagated by budding in 1994 and established in a randomized evaluation plot complete with 'Golden Delicious' (unpatented), and 'Sunrise' as reference varieties. Sensory evaluation panels began in 1995. Controlled grower trials under test agreement have been established in British Columbia. '8S-4-33' was named 'Silken' in 1997 by Dr. H.A. Quamme.

Distinguishing Characteristics

The variety 'Silken', is an early to mid-season apple, maturing about the 1st to 6th of September at Summerland. The fruit is medium sized, averaging 7.5 cm in diameter and 180 to 220 grams in weight. The skin of the fruit is creamy ivory to pale yellow, has a bright luster, is translucent and has few non-prominent lenticels. Some stem bowl russeting is present, but it does not usually extend past the shoulders of the fruit. The fruit of 'Silken' is oblong to globose conical and slightly truncate in form, slightly ribbed and very slightly irregular, with distinct lobing at the calyx end. The fruit stalk is moderate to long, measuring 22.5 mm on average. The fruit flesh of 'Silken' is crisp, firm (a pressure of 14–15 lbs at maturity), juicy and white. The soluble solids content of 'Silken' at maturity is about 14%. Initial storage assessments indicate that 'Silken' stores for 2 months in air storage and 4 months in controlled atmosphere (CA) storage. The tree habit of 'Silken' is moderately vigorous and spreading. The tree is very precocious and productive.

Parent Plants

'Silken' is the result of a controlled cross of the seed parent 'Honeygold' and the pollen parent 'Sunrise'. 'Honeygold' is the result of a cross of 'Golden Delicious' and 'Haralson' introduced by the University of Minnesota in 1969. Both 'Golden Delicious' and 'Haralson' are older established commercial varieties. 'Honeygold' matures in mid- to late season. 'Honeygold' has medium-sized oblate to roundish conic shaped fruit; the skin is yellow with a dull finish and many large, conspicuous russeted lenticels. 'Honeygold' has cream colored, crisp, juicy flesh that deteriorates quickly in storage. 'Silken' differs from 'Honeygold' in that 'Silken' matures in early to mid-season, has oblong to globose conical shaped fruit with ivory to soft yellow skin, a lustrous finish and a few non-prominent lenticels.

'Sunrise' is a cross of 10C-10-19 ('McIntosh'×'Golden Delicious') ×'PCF-3-120' and was introduced by the Agriculture and Agri-Food Canada, Summerland Research Centre breeding program in 1994. 'Sunrise' is a large, early season apple, oval to round in shape, with pink/red skin on a pale yellow background. 'Silken' differs from 'Sunrise' differs from 'Sunrise' in the 'Silken' has ivory to soft yellow skin, matures at a later date, and has an oblong to globose conical fruit.

SUMMARY OF THE INVENTION

The new and distinct variety of Malus fruiting apple tree, 'Silken', was bred in 1982 at the Pacific Agri-Food Research Centre in Summerland, British Columbia, Canada. The variety has been established and is being maintained at the research facility. Evaluations began upon fruiting.

The variety is stable with no variations occurring, and demostrates significant differences from its parents in that it has creamy ivory to pale yellow skin, is globose conical to oblong and slightly truncate in form, slightly ribbed, very slightly irregular in shape, with a distinctly wide, lobed, clean calyx. The fruit is very sweet and juicy, and the tree very precocious and productive. 'Silken' has continued to yield good crops annually. The variety matures in early to mid-season, with harvest dates around September 1st to 6th in Summerland. 'Silken' was asexually propagated (by budding) in 1985 and established in a seedling evaluation plot. 'Silken' first fruited in 1986 and has been evaluated from then until 1996. The tree habit is spreading with spur-type branches, moderately vigorous, and produces heavy crops annualy. 'Silken' does not shown any unusual susceptibility to any diseases including mildew, fireblight and apple scab. The test plantings also contained the standard varieties 'Golden Delicious' and 'Sunrise' for comparison to 'Silken'. 'Silken' differs from 'Golden Delicious' in that 'Golden Delicious' is a mid to late season variety with greenish yellow skin, prominent, russeted lenticels and a truncate shape. While 'Silken' matures in early to mid-season, has ivory to soft yellow, translucent skin, with few non prominent lenticels and an oblong to globose truncate shape. 'Silken' differs from 'Sunrise' in that 'Sunrise' matures about 2 to 3 weeks before 'Silken' and has a green/yellow background skin color with 40% to 50% pink/red overcolor.

BRIEF DESCRIPTION OF THE DRAWINGS

The accompanying photographs show the mature fruit, limb and leaves of 'Silken'.

The photograph on sheet 1 shows the typical mature fruit positioned to display stem end, calyx end and side view. The photograph on sheet 1 also displays a cross-sectional view to reveal the internal arrangement of the core, seeds and locules, and a longitudinal section to show the eye basin, stem bowl, core, and the color of the flesh and seeds. The photographs on sheet 2 depict mature fruit on the tree and at harvest and the photograph on sheet 3 illustrates the growth habit of a fruit bearing tree.

TRIALS AND EVALUATIONS

Upon selection from the seedling stage the new variety was asexually reproduced in 1984 by budding and designated '8S-4-33'. '8S-4-33' was planted in variety blocks, complete with standards at the Pacific Agri-Food Research Centre Summerland orchards, in 1986. The reproductions exhibited no variations and the fruit and plant characteristics were true to the original tree in all respects. The variety 'Silken' ('8S-4-33') was planted in close proximity to the reference varieties 'Golden Delicious' and 'Sunrise'. The variety has been observed and evaluated since 1986. Controlled grower trials, under test agreements, have been established in British Columbia and in selected sites in the United States.

'Silken' was tested in sensory evaluation panels in 1995 and 1996. The standards used in the sensory evaluation panels were 'Royal Gala' (U.S. Plant Pat. No. 4121) and 'Sunrise' in 1995 and 'Royal Gala' and 'McIntosh' in 1996. 'Silken' and 'Royal Gala' did not differ significantly in the intensity of sensory qualities in 1995 or 1996, and found equally acceptable in appearance, texture and flavor. 'Silken' was rated significantly higher than 'Sunrise' in appearance and texture on a hedonic scale in 1995, and firmer and juicier than 'Sunrise' on sensory scales. 'Silken' was also rated significantly higher than 'McIntosh' in appearance, flavor and texture on a hedonic scale in 1996, and significantly higher in crispness, hardness, juiciness, and sweetness on sensory scales. In sensory evaluation panels in 1995 for apples maturing up to mid-September, 'Silken' was rated as the best apple for appearance, texture and flavor in the Summerland collection.

BOTANICAL DESCRIPTION OF THE PLANT

'Silken'

Genus: Malus.
Species: domestica.
Market class: Dessert.
Parentage: 'Honeygold'×'Sunrise'.

'Honeygold'

Genus: Malus.
Species: domestica.
Market class: Dessert.
Parentage: 'Golden Delicious'×'Haralson'.

'Sunrise'

Genus: Malus.
Species: domestica.
Market class: Dessert.
Parentage: '10C-10-19' ('McIntosh'×'Golden Delicious')× 'PCF-3-120'.

The following is a detailed desciption of the new variety, with color terminology in accordance with The Royal Horticultural Society (R.H.S.) Colour Chart, except where general color terms of ordinary dictionary significance are sutible.

Pomological Characteristics

'Silken'

Fruit end use: Dessert.

Tree: Trees observed were of the same age, on M9 rootstock and in close proximity.

*Vigor.*—Non-vigorous.
*Habit.*—Spreading.
*Branch frequency.*—Medium.
*Branch strength.*—Intermediate.
*Angle of bearing branches.*—50–90 degrees.
*Predominance of bearing.*—Spurs.

Shoot characteristics: Observations are means of 10 one-year-old dormant shoots in 1996.

*Pubescence* (*on upper half*).—Medium to strong.
*Shine of bark.*—Medium.
*Mean diameter* (*center of middle internode*).—5 mm.
*Mean internode length.*—30 mm.
*Density of lenticels* (*middle third of shoot*).—Medium.
*Size of lenticels.*—Large.
*Predominant color* (*on sunny side*).—Reddish brown.
*Position of bud on shoot.*—Appressed.
*Shape of bud.*—Pointed.

Flower characteristics: Observations are means of 10 flowers.

*Type.*—Single.
*Size*(*pressed flat*).—56 mm.
*Color of bud* (*balloon stage*).—63B/155D (R.H.S.).
*Bud burst.*—Before 'McIntosh' and after'Sunrise'.
*Petal shape.*—Broad elliptic.
*Petal margins.*—Not touching.

Leaf characteristics: 4th to 6th fully expanded leaf. Measurements are mean of 10 leaves.

*Shape at tip of* (*cross section*).—Concave.
*Pubescence of upper side.*—Weak.
*Color on upper side of leaf.*—137A (R.H.S.).
*Veins.—Some anthocyanin evident.*
*Leaf orientation.*—Up and out.
*Leaf length.*—Mean: 86 mm. Range: 74–100 mm.
*Leaf width.*—Mean: 58 mm. Range: 50–68 mm.
*Leaf blade ratio* (*length/width*).—1.5.
*Petiole length.*—Means: 22.5 mm. Range: 20–25 mm.
*Ratio leaf length/petiole length.*—3.8. Glossiness of upper side.—Medium. *Pubescence.*—Slightly pubescent lower side.
*Stipule size.*—Mean: 14.6 mm. Range: 12–20 mm.

Fruit characteristics: Measurements are the mean of 10 mature fruits.

*Size* (*diameter*).—7.6 cm.
*Average fruit weight.*—180–220 g.
*Shape.*—Oblong to globose conical.
*Symmetry* (*side view*).—Slightly asymmetrical.
*Ribbing.*—Slight.
*Distal end lobing.*—Distinct.
*Depth of eye basin.*—13 mm.
*Width of eye basin.*—30 mm.
*Sepal spacing.*—Touching to overlapping.
*Thickness of stalk.*—2.3 mm.
*Stalk cavity width.*—34 mm.
*Stalk cavity depth.*—16.3 mm.
*Stalk length.*—22 mm.
*Surface.*—Smooth.
*Bloom of skin.*—Absent.
*Waxiness of skin.*—Slight.
*Translucency of skin.*—Translucent.
*Ground color.*—Creamy ivory to pale green (8C R.H.S.).
*Amount of overcolor of skin.*—Less than 10%.
*Overcolor of skin.*—Pink (46A).
*Type of overcolor.*—Faded pink.
*Position of russet.*—Stem bowl, does not exceed shoulders.
*Amount of russet.*—Most of stem bowl.
*Size of lenticels on fruit.*—Small.
*Prominence of lenticels.*—Very slight.
*Distinctness of core line* (*cross section*).—Weak.
*Aperture of locules.*—Open, small and shallow.
*Fruit set* (*yield efficiency*).—High.
*Maturity date at Summerland, B.C..*—1st week of September.
*Seed color at maturity.*—Brown.
*Soluble solids* (%).—13.8% at harvest.
*Titratable acidity.*—500–600 mg malic acid per 100 ml juice.
*Juiciness.*—Very juicy.
*Flesh firmness without skin* (*penetrometer*).—15–16 lbs. at havest.
*Browning of flesh* (1 *hr. after cutting*).—Low.

Storage life of fruit:

*Air.*—2 months.
*Controlled atmosphere.*—4 months.

I claim:

1. A new and distinct variety of apple tree, originating from a controlled cross of 'Honeygold'×'Sunrise' substantially as illustrated and described herein, which is most similar to 'Golden Delicious' and characterized as to novelty by the ivory to pale yellow skin color, bright luster, oblong to globose conical and slightly truncate shape, distinct calyx lobing, and the unique combination of taste, texture and juiciness which are different from other dessert quality apples.

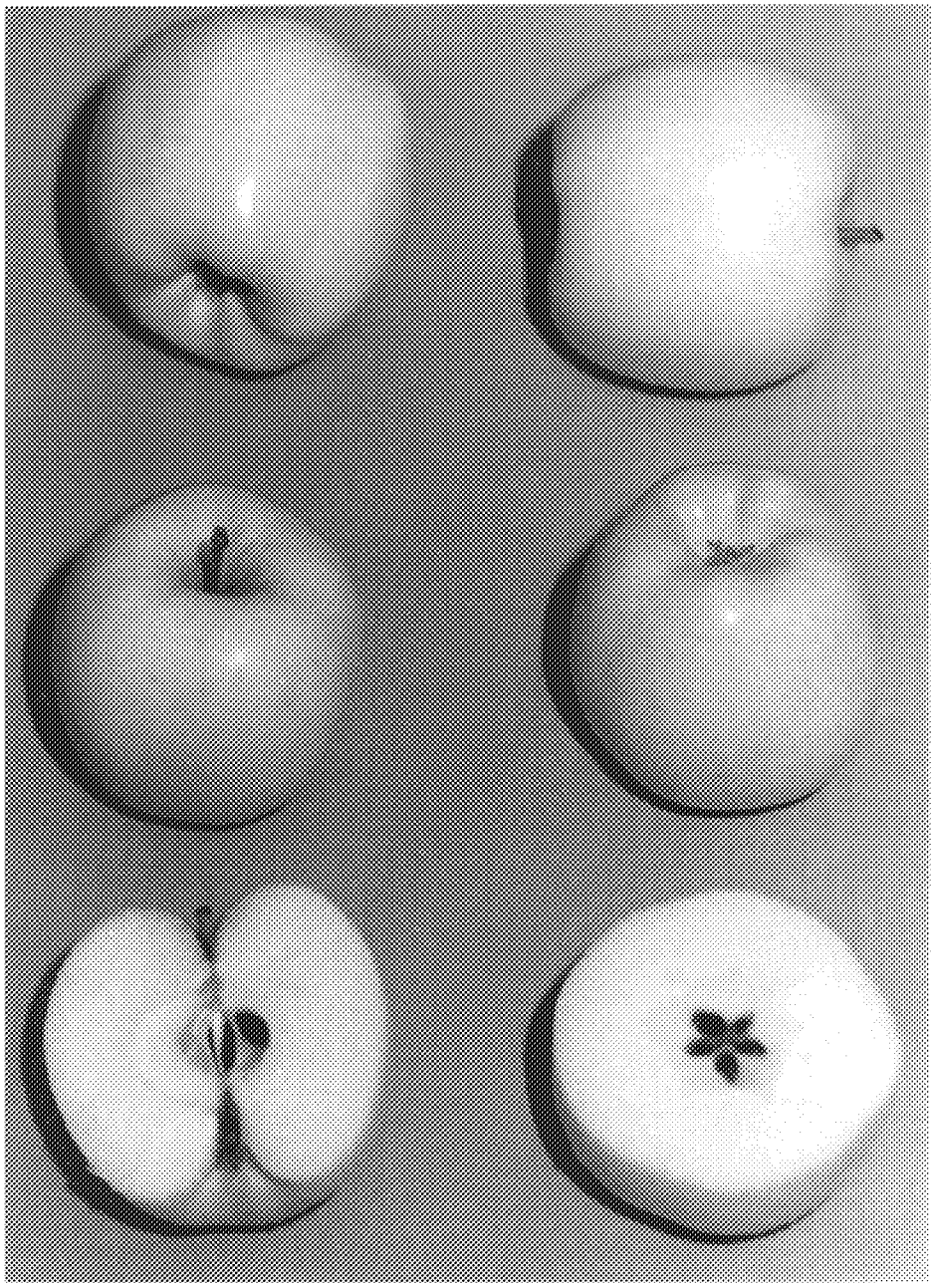

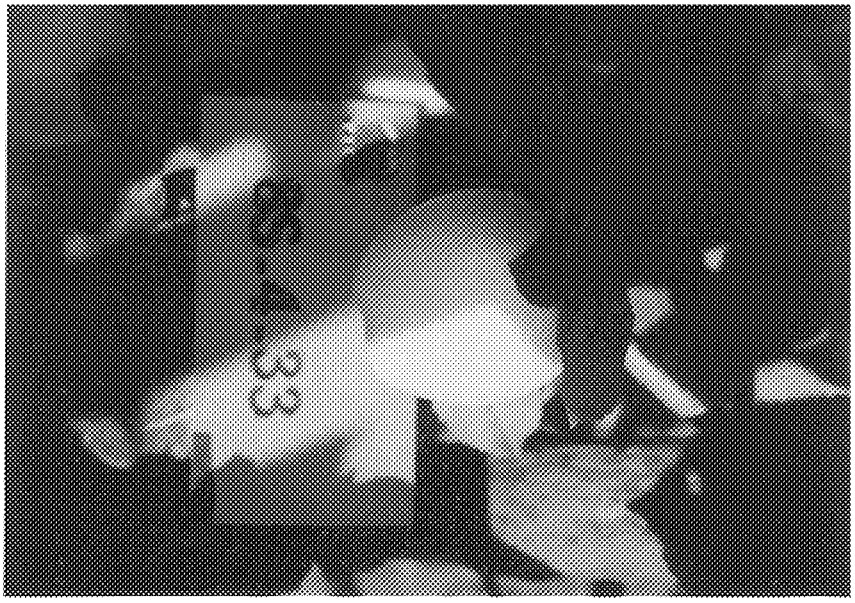
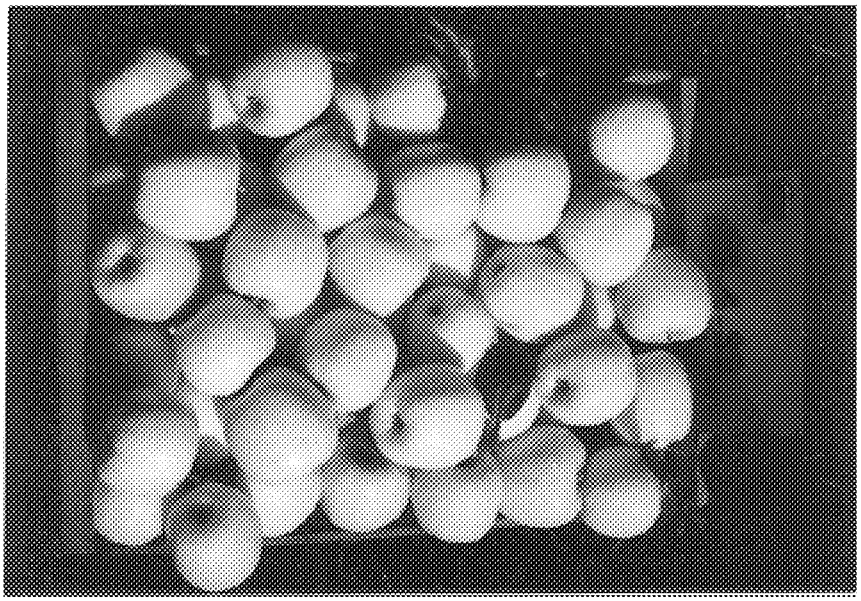

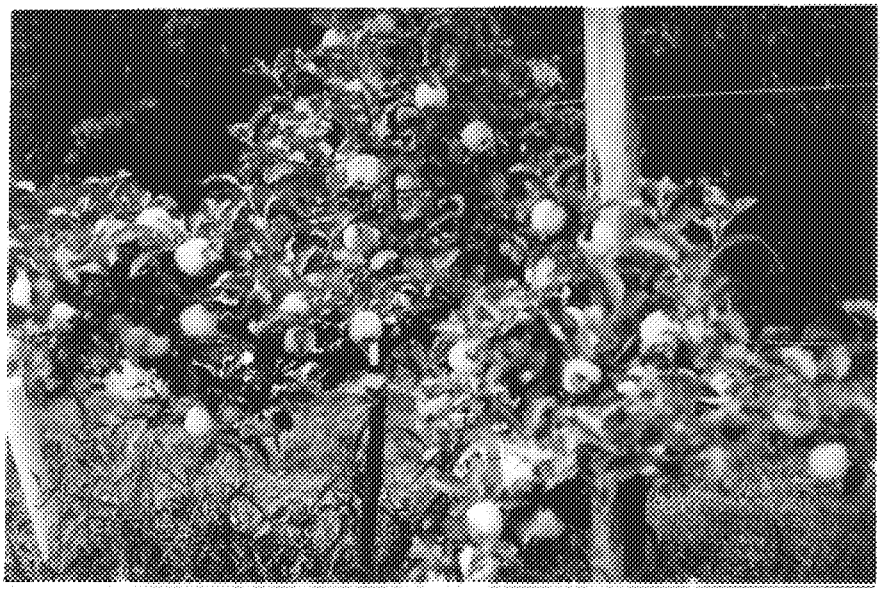

* * * * *